(12) United States Patent
Kotani et al.

(10) Patent No.: US 10,221,951 B2
(45) Date of Patent: Mar. 5, 2019

(54) VALVE AND FLUID CONTROL APPARATUS

(71) Applicant: Murata Manufacturing Co., Ltd., Nagaokakyo-shi, Kyoto-fu (JP)

(72) Inventors: Kenichi Kotani, Nagaokakyo (JP); Takenobu Maeda, Nagaokakyo (JP); Atsuhiko Hirata, Nagaokakyo (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 0 days.

(21) Appl. No.: 15/919,263

(22) Filed: Mar. 13, 2018

(65) Prior Publication Data

US 2018/0202562 A1   Jul. 19, 2018

Related U.S. Application Data

(63) Continuation of application No. 15/462,967, filed on Mar. 20, 2017, now Pat. No. 9,951,879, which is a (Continued)

(30) Foreign Application Priority Data

Apr. 19, 2012 (JP) .................................. 2012-095722

(51) Int. Cl.
| | |
|---|---|
| *F16K 7/17* | (2006.01) |
| *F04B 43/04* | (2006.01) |
| *F04B 53/10* | (2006.01) |
| *F16K 11/02* | (2006.01) |
| *F16K 11/10* | (2006.01) |

(Continued)

(52) U.S. Cl.
CPC ................. *F16K 7/17* (2013.01); *A61B 5/022* (2013.01); *F04B 43/043* (2013.01); *F04B 53/106* (2013.01); *F16K 11/022* (2013.01); *F16K 11/105* (2013.01); *F16K 11/22* (2013.01); *F16K 15/144* (2013.01); *F16K 31/128* (2013.01); *F16K 31/1266* (2013.01)

(58) Field of Classification Search
CPC ........ F16K 7/17; F16K 11/022; F16K 15/144; F16K 31/1266; F16K 31/128; F04B 43/043; F04B 53/106
See application file for complete search history.

(56) References Cited

U.S. PATENT DOCUMENTS

| | | | | |
|---|---|---|---|---|
| 3,245,426 | A | * | 4/1966 | Kreuter .................. F15B 13/00 137/112 |
| 2005/0221147 | A1 | * | 10/2005 | Shioya .................. F16K 31/004 429/443 |
| 2013/0058819 | A1 | * | 3/2013 | Kodama ............... F04B 43/043 417/479 |

OTHER PUBLICATIONS

Kotani et al., "Valve and Fluid Control Apparatus", U.S. Appl. No. 15/462,967, filed Mar. 20, 2017.

* cited by examiner

*Primary Examiner* — P. Macade Nichols
(74) *Attorney, Agent, or Firm* — Keating & Bennett, LLP

(57) ABSTRACT

A valve includes a lower valve housing, a diaphragm, and an upper valve housing. A top surface of a piezoelectric pump is bonded to a bottom surface of the lower valve housing. A circular hole portion is provided in a central portion of a region of the diaphragm that opposes a projecting portion of the lower valve housing. The diaphragm is bonded to the upper valve housing and the lower valve housing, and a divided interior of a valve housing configures a first lower valve chamber, a second lower valve chamber, a first upper valve chamber, and a second upper valve chamber. A groove is located in a wall portion of the upper valve housing that opposes the diaphragm in the first upper valve chamber.

11 Claims, 15 Drawing Sheets

Related U.S. Application Data continuation of application No. 14/516,814, filed on Oct. 17, 2014, now Pat. No. 9,631,730, which is a continuation of application No. PCT/JP2013/055068, filed on Feb. 27, 2013.

(51) Int. Cl.
*F16K 15/14* (2006.01)
*F16K 31/126* (2006.01)
*F16K 31/128* (2006.01)
*A61B 5/022* (2006.01)
*F16K 11/22* (2006.01)

VALVE AND FLUID CONTROL APPARATUS

BACKGROUND OF THE INVENTION

1. Field of the Invention

The present invention relates to valves that prevent backflow of a fluid, and to fluid control apparatuses provided with such valves.

2. Description of the Related Art

Japanese Unexamined Patent Application Publication No. 2002-106469 discloses a diaphragm pump provided with a valve.

FIG. 14 is an exploded perspective view illustrating a diaphragm pump 90 according to Japanese Unexamined Patent Application Publication No. 2002-106469. FIG. 15 is a cross-sectional view illustrating the primary components of the diaphragm pump 90 shown in FIG. 14.

The diaphragm pump 90 is configured of a housing 900 provided with an exhaust channel 901 and an intake channel 902, and a diaphragm 910 for forming a pump chamber with the housing 900. The housing 900 is configured of an upper housing portion 930, a lower housing portion 940, and a diaphragm (film) 920.

An intake channel groove portion 942 through which air is sucked into the pump chamber from outside of the housing 900, an exhaust channel groove portion 941 through which air is exhausted from the pump chamber to the outside of the housing 900, an approximately cylindrical recess portion 945, an approximately cylindrical recess portion 946, a cylindrical platform 947 located in the center of the recess portion 946, a projecting portion 944, and a projecting portion 943 are provided in the lower housing portion 940.

The exhaust channel 901, the intake channel 902, a recess portion 935 that opposes the recess portion 945, a recess portion 936 that opposes the recess portion 946, a cylindrical platform 937 located in the center of the recess portion 935, a projecting portion 934 that is bonded to the projecting portion 944, and a projecting portion 933 that is bonded to the projecting portion 943 are provided in the upper housing portion 930. The diaphragm 910 is bonded, using an adhesive, to an outer edge portion in an upper surface of the upper housing portion 930, the outer edge portion being located further toward an outer side portion than the exhaust channel 901 and the intake channel 902.

A hole portion 921A that faces the platform 947 and a hole portion 921B that faces the platform 937 are provided in the diaphragm 920.

The upper housing portion 930 and the lower housing portion 940 are bonded to each other, with the diaphragm 920 located therebetween, using an adhesive. Accordingly, the diaphragm 920 is sandwiched between the upper housing portion 930 and the lower housing portion 940.

As shown in FIG. 15, an intake valve is configured by the recess portions 936 and 946, the platform 947, and the periphery of the hole portion 921A and the hole portion 921A in the diaphragm 920. The intake valve allows a fluid to flow from the intake channel groove portion 942 side toward the diaphragm 910 side but prevents the fluid from flowing from the diaphragm 910 side toward the intake channel groove portion 942 side.

Meanwhile, an exhaust valve is configured by the recess portions 935 and 945, the platform 937, and the periphery of the hole portion 921B and the hole portion 921B in the diaphragm 920. The exhaust valve allows the fluid to flow from the diaphragm 910 side toward the exhaust channel groove portion 941 side but prevents the fluid from flowing from the exhaust channel groove portion 941 side toward the diaphragm 910 side.

The diaphragm pump 90 configured as described above is operated by causing the diaphragm 910 to bend.

When the diaphragm pump 90 is driven, the periphery of the hole portion 921A in the diaphragm 920 separates from the platform 947, and the periphery of the hole portion 921B in the diaphragm 920 separates from the platform 937. As a result, the exhaust valve and intake valve each open, and air flows in from the intake channel groove portion 942 and is exhausted from the exhaust channel groove portion 941.

However, in the diaphragm pump 90, there are cases, during driving, where the pressure on the diaphragm 910 side of the diaphragm 920 increases suddenly. In such a case, in the exhaust valve, the periphery of the hole portion 921B in the diaphragm 920 will separate by a significant amount from the platform 937 and make contact with the recess portion 945 in the lower housing portion 940. In other words, the hole portion 921B is covered by the lower housing portion 940 and the exhaust valve is blocked.

Accordingly, with the diaphragm pump 90, there is a problem in that the diaphragm 920 in the exhaust valve deforms greatly and the transport of fluid will stop in the case where the pressure acting on the diaphragm 910 side of the diaphragm 920 is much higher.

SUMMARY OF THE INVENTION

Preferred embodiments of the present invention provide a valve, which blocks the flow of a fluid from one main surface side of a diaphragm to another main surface side of the diaphragm, that prevents the transport of fluid from stopping even in the case where pressure on the other main surface side of the diaphragm has become extremely high, as well as a fluid control apparatus provided with such a valve.

A valve according to a preferred embodiment of the present invention includes a valve housing provided with a first opening portion and a second opening portion, and a diaphragm, provided with a hole portion, that divides the interior of the valve housing so as to configure, in the valve housing, a first valve chamber configured to communicate with the first opening portion and a second valve chamber configured to communicate with the second opening portion, the hole portion is covered by a periphery of the hole portion in the diaphragm making contact with the valve housing in the first valve chamber, and a flow channel formation portion is provided in at least a portion of a wall portion of the valve housing that opposes the diaphragm in the second valve chamber, the flow channel formation portion defining a flow channel connecting the first valve chamber and the second valve chamber when the periphery of the hole portion in the diaphragm makes contact with the wall portion.

In this configuration, the first opening portion preferably is connected to a pump, for example. The second opening portion preferably is connected to a fluid holding portion such as a cuff for blood pressure measurement, for example.

Even in such a configuration, when the second valve chamber faces one main surface of the diaphragm and the first valve chamber faces another main surface of the diaphragm, there are cases where a pressure in the first valve chamber becomes much higher than a pressure in the second valve chamber, causing the diaphragm to deform greatly and the periphery of the hole portion in the diaphragm to separate greatly from a portion of the valve housing.

According to this configuration, the flow channel formation portion is provided in at least a portion of the wall portion of the valve housing that opposes the diaphragm. Accordingly, even if the periphery of the hole portion in the diaphragm makes contact with the wall portion of the valve housing, the first opening portion and the second opening portion are able to communicate via the first valve chamber, the hole portion, the flow channel formation portion, and the second valve chamber.

As a result, the hole portion in the diaphragm will not be covered by the wall portion of the valve housing, and a fluid is able to flow from the first valve chamber, through the hole portion, and into the second valve chamber. In other words, a flow channel for the fluid is secured.

Therefore, according to this configuration, in a valve that blocks the flow of a fluid from one main surface side of a diaphragm to another main surface side of the diaphragm, the transport of fluid is prevented from stopping even in the case where pressure on the other main surface side of the diaphragm has become extremely high. Furthermore, according to this configuration, a fluid flow channel is secured even if the distance between the diaphragm and the wall portion of the valve housing is reduced, and thus the profile of the valve is able to be reduced as well.

It is preferable that the diaphragm be anchored to the valve housing so that the periphery of the hole portion in the diaphragm makes contact with or separates from the valve housing due to a difference between a pressure in the first valve chamber and a pressure in the second valve chamber.

It is preferable that the flow channel formation portion be a groove and that the groove be configured so as to extend from a region of the wall portion that opposes the hole portion in the diaphragm to a region of the wall portion that opposes a portion of the diaphragm aside from the hole portion.

According to this configuration, the hole portion in the diaphragm is still able to communicate with the second valve chamber via the groove even if the pressure in the first valve chamber has become much higher than the pressure in the second valve chamber, the diaphragm has deformed greatly, and the diaphragm makes contact with a region of the valve housing across a wide range as a result.

Accordingly, in this configuration as well, the hole portion in the diaphragm will not be covered, and the fluid still is able to flow from the first valve chamber, through the hole portion, and into the second valve chamber. In other words, a flow channel for the fluid is secured. Therefore, according to this configuration, the transport of fluid is further suppressed or prevented from stopping.

It is preferable that the flow channel formation portion be a projection and that the projection be arranged so as to extend from a region of the wall portion that opposes the hole portion in the diaphragm to a region of the wall portion that opposes a part of the diaphragm aside from the hole portion.

According to this configuration, the hole portion in the diaphragm is configured to communicate directly with the second valve chamber even if the pressure in the first valve chamber has become much higher than the pressure in the second valve chamber, the diaphragm has deformed greatly, and the diaphragm makes contact with a region of the valve housing across a wide range as a result.

Accordingly, in this configuration as well, the hole portion in the diaphragm will not be covered, and the fluid is able to flow from the first valve chamber, through the hole portion, and into the second valve chamber. In other words, a flow channel for the fluid is secured. Therefore, according to this configuration, the transport of fluid is further suppressed or prevented from stopping.

It is preferable that a width of the flow channel formation portion be smaller than a diameter of the hole portion in the diaphragm.

In the case where the width of the flow channel formation portion is greater than the diameter of the hole portion in the diaphragm, there is a risk that the periphery of the hole portion in the diaphragm will make contact with the flow channel formation portion and the hole portion will be covered as a result.

However, according to this configuration, the width of the flow channel formation portion preferably is smaller than the diameter of the hole portion in the diaphragm, and thus the periphery of the hole portion in the diaphragm is prevented from making contact with the flow channel formation portion and the hole portion is prevented from being covered as a result. Therefore, according to this configuration, the transport of fluid is further suppressed or prevented from stopping.

It is preferable that the valve housing be provided with a projecting portion that projects toward the diaphragm in the first valve chamber, and that the periphery of the hole portion in the diaphragm make contact with the projecting portion.

According to this configuration, the periphery of the hole portion in the diaphragm will separate from the projecting portion and enable the first opening portion and the second opening portion to communicate with each other in the case where, for example, the pressure in the first valve chamber is higher than the pressure in the second valve chamber. Meanwhile, the periphery of the hole portion in the diaphragm will make contact with the projecting portion and prevent the first opening portion and the second opening portion from communicating with each other in the case where, for example, the pressure in the first valve chamber is lower than the pressure in the second valve chamber.

It is preferable that the first valve chamber, the second valve chamber, and the projecting portion each have cylindrical or substantially cylindrical shapes when viewed from above in a direction perpendicular to the diaphragm.

According to this configuration, the first valve chamber and the second valve chamber have circular or substantially circular outer shapes, and thus uniform tension acts on the diaphragm (and particularly in the periphery near the hole portion). Accordingly, the diaphragm is prevented from making contact with the hole portion thereof tilted relative to the projecting portion, the hole portion in the diaphragm is prevented from shifting relative to the projecting portion in the horizontal direction, and so on. Therefore, according to this configuration, the opening/closing of the valve is carried out with certainty.

It is preferable that the valve further include a first adhesive sheet and a second adhesive sheet, and that the valve housing include a first valve housing in which the first opening portion is provided and a second valve housing in which the second opening portion is provided, the first valve housing and the diaphragm be bonded to each other by the first adhesive sheet and the diaphragm and the second valve housing be bonded to each other by the second adhesive sheet, a first through-hole be provided in a region of the first adhesive sheet that faces the first valve chamber and a second through-hole be provided in a region of the second adhesive sheet that faces the second valve chamber, an outer circumference of the first through-hole be greater than an outer circumference of the projecting portion and smaller than an outer circumference of the first valve chamber, and an outer circumference of the second through-hole be greater than the outer circumference of the projecting portion and smaller than an outer circumference of the second valve chamber.

According to this configuration, a portion of the first adhesive sheet is located within the first valve chamber, and a portion of the second adhesive sheet is located within the second valve chamber. Accordingly, the first adhesive sheet and the second adhesive sheet bond the first and second valve housings and the diaphragm, and foreign objects present in the respective valve chambers are caught.

Therefore, according to this configuration, even if foreign objects have entered into the valve, for example, erroneous operations caused by such foreign objects are prevented.

Furthermore, a fluid control apparatus according to another preferred embodiment the present invention has the following configuration.

It is preferable that the fluid control apparatus include a pump provided with an ejection hole and the valve according to any one of the preferred embodiments of the present invention described above, and that the first opening portion of the valve be connected to the ejection hole of the pump, and the second opening portion of the valve be connected to a fluid holding portion that holds a fluid.

According to this configuration, by including the valve according to any one of the preferred embodiments of the present invention described above, the fluid control apparatus that includes the valve achieves the same effects as those described thus far.

Note that in this configuration, the pump preferably includes, for example, an actuator in which a peripheral portion is unrestricted or substantially unrestricted and that bends and vibrates from a central portion to the peripheral portion, and a planar portion disposed near to and opposing the actuator, and one or a plurality of ventilation holes are provided in an actuator-opposing region of the planar portion that opposes the actuator. According to this configuration, a pump that is capable of high pressures and a high flow rate while being small and having a low profile is used, which makes it possible to provide an even smaller, low-profile fluid control apparatus.

According to various preferred embodiments of the present invention, in a valve that blocks the flow of a fluid from one main surface side of a diaphragm to the other main surface side of the diaphragm, the transport of fluid is prevented from stopping even in the case where pressure on the other main surface side of the diaphragm has become extremely high.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

First Preferred Embodiment

A fluid control apparatus 100 according to a first preferred embodiment of the present invention will be described hereinafter.

Figure 1:
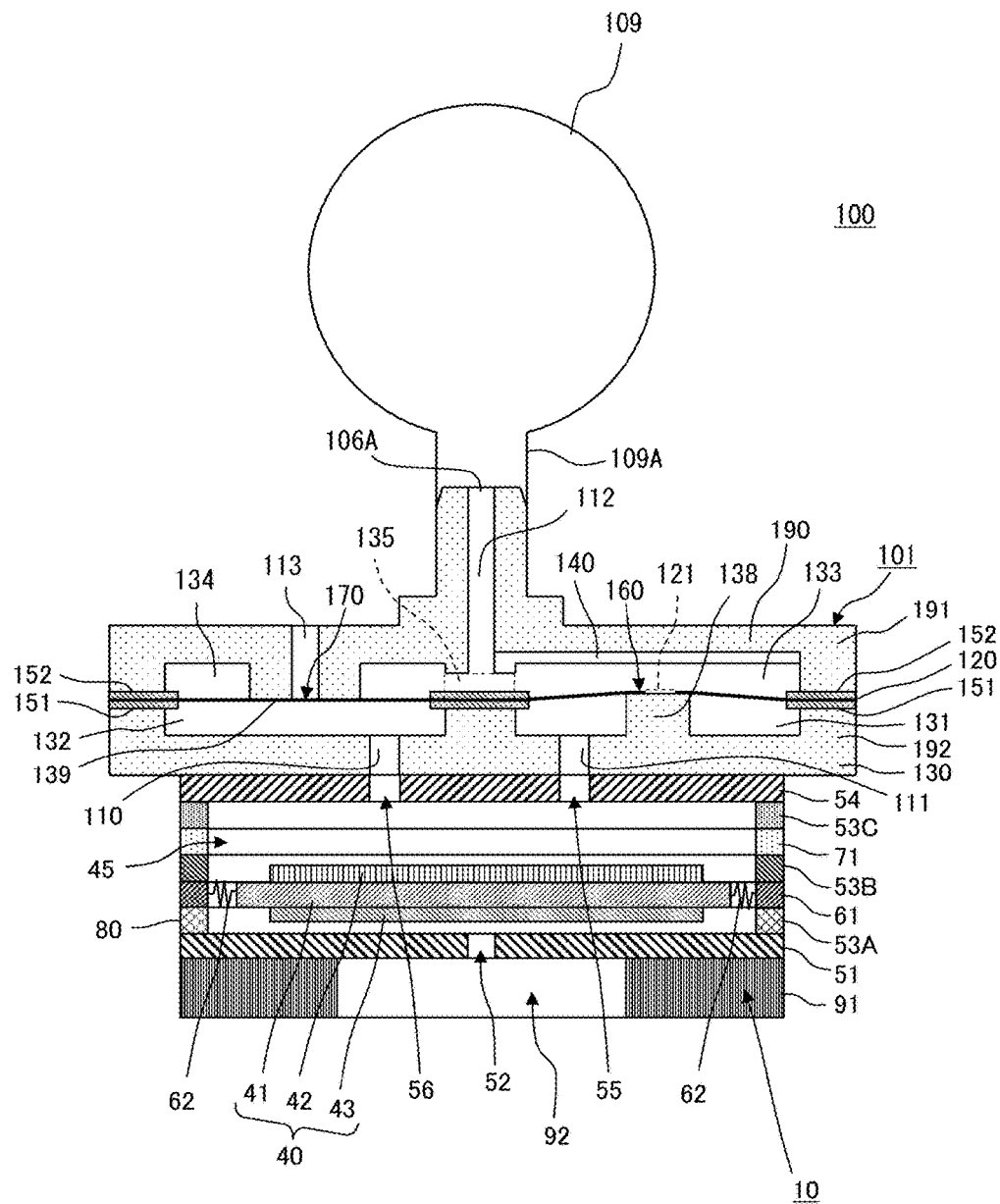
FIG. 1 is a cross-sectional view illustrating the primary components of a fluid control apparatus 100 according to a first preferred embodiment of the present invention.

FIG. 1 is a cross-sectional view illustrating the primary components of the fluid control apparatus 100 according to the first preferred embodiment of the present invention.

The fluid control apparatus 100 includes a piezoelectric pump 10 and a valve 101. The valve 101 is connected to the piezoelectric pump 10 by a top surface of the piezoelectric pump 10 being bonded to a bottom surface of the valve 101.

The valve 101 is provided with a cuff connection port 106A that enables communication with a manchette rubber tube 109A of a cuff 109. The fluid control apparatus 100 is connected to the cuff 109 by the manchette rubber tube 109A of the cuff 109 being attached to the cuff connection port 106A of the valve 101.

Note that the cuff 109 corresponds to a "fluid holding portion".

The structure of the piezoelectric pump 10 and the valve 101 will now be described in detail. First, the structure of the piezoelectric pump 10 will be described in detail using FIGS. 2 and 3.

Figure 2:
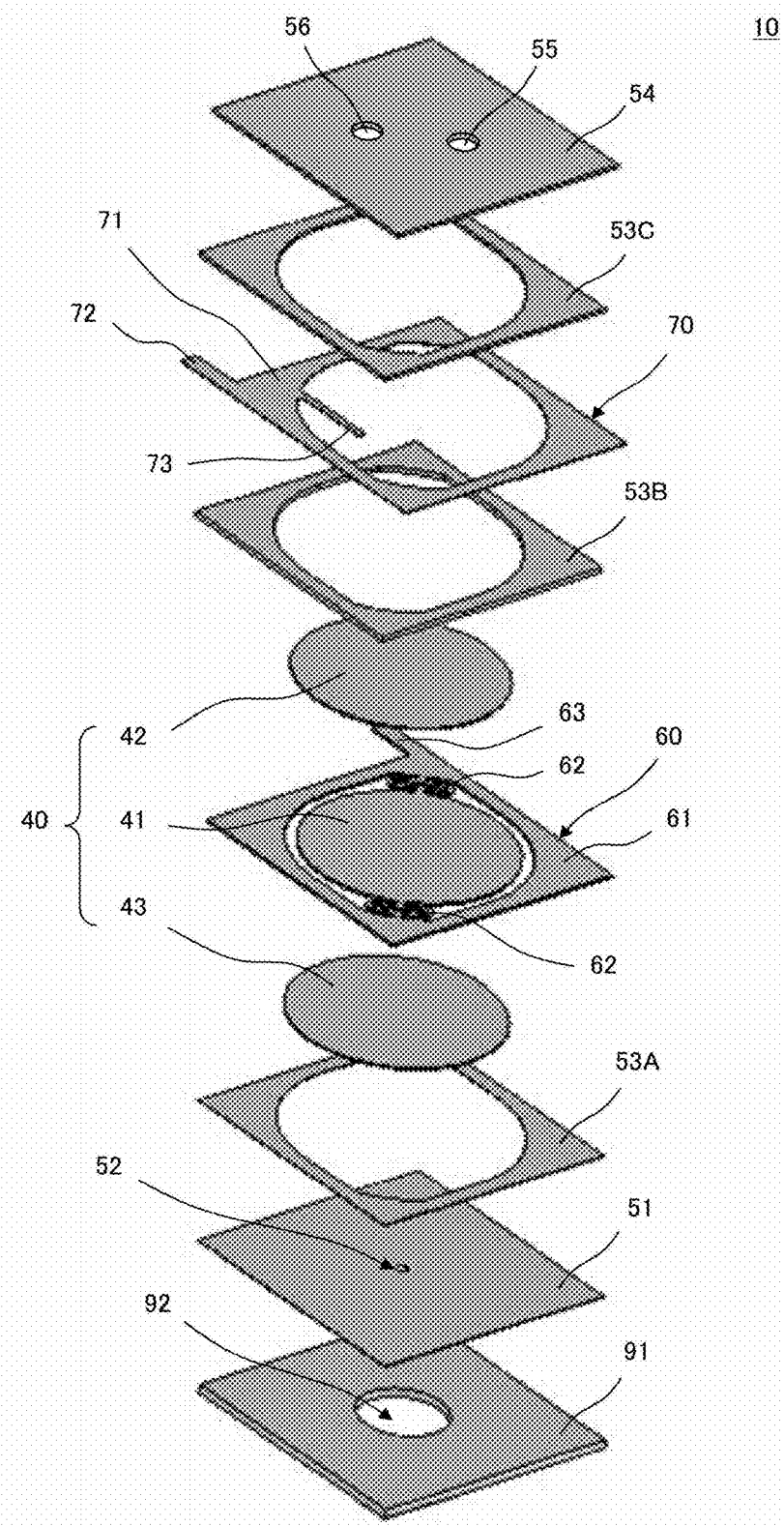
FIG. 2 is an exploded perspective view illustrating a piezoelectric pump 10 shown in FIG. 1.
Figure 3:
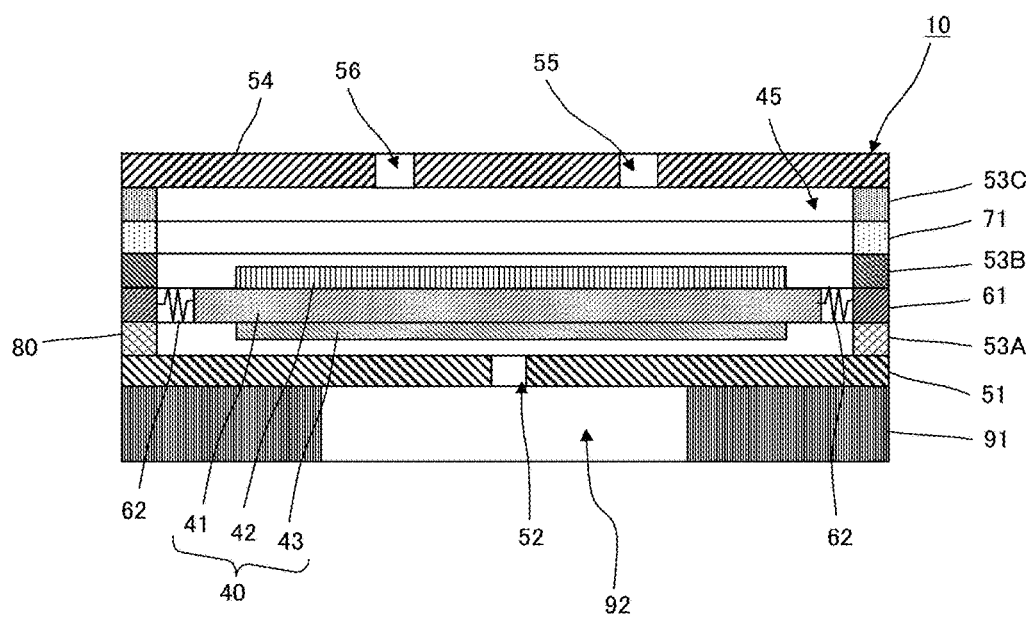
FIG. 3 is a cross-sectional view illustrating the primary components of the piezoelectric pump 10 shown in FIG. 1.

FIG. 2 is an exploded perspective view illustrating the piezoelectric pump 10 shown in FIG. 1, and FIG. 3 is a cross-sectional view illustrating the primary components of the piezoelectric pump 10. The piezoelectric pump 10 has a structure in which a substrate 91, a flexible plate 51, a spacer 53A, a reinforcement plate 43, a vibrating plate unit 60, a piezoelectric element 42, a spacer 53B, an electrode conducting plate 70, a spacer 53C, and a cover plate 54 are stacked in that order.

The piezoelectric element 42 is bonded and anchored to a top surface of a circular or substantially circular plate-shaped vibrating plate 41, the reinforcement plate 43 is affixed to a bottom surface of the vibrating plate 41, and a circular or substantially circular piezoelectric actuator 40 is configured by the vibrating plate 41, the piezoelectric element 42, and the reinforcement plate 43. The piezoelectric element 42 is configured of a PZT-based ceramic material, for example.

Here, by configuring the vibrating plate 41 of a metal plate having a greater coefficient of linear expansion than the piezoelectric element 42 and the reinforcement plate 43 and bonding the vibrating plate 41 through thermosetting, an appropriate amount of compressive stress can be left in the piezoelectric element 42 without the piezoelectric actuator 40 warping as a whole, which makes it possible to prevent the piezoelectric element 42 from breaking.

For example, it is preferable for the vibrating plate 41 to be configured of a material that has a high coefficient of linear expansion, such as phosphor bronze (C5210) or stainless steel SUS301, and for the reinforcement plate 43 to be configured of 42 nickel, 36 nickel, stainless steel SUS430, or the like.

Note that the vibrating plate 41, the piezoelectric element 42, and the reinforcement plate 43 may be disposed in order from the piezoelectric element 42, to the reinforcement plate 43, and to the vibrating plate 41. In this case as well, the coefficient of linear expansion is adjusted by reversing the materials of the reinforcement plate 43 and the vibrating plate so that an appropriate compressive stress remains in the piezoelectric element 42.

A frame plate 61 is provided in the periphery of the vibrating plate 41, and the vibrating plate 41 is connected to the frame plate 61 via connecting portions 62. The connecting portions 62 are provided in a thin ring shape, for example, and have an elastic structure in which elasticity is provided at a low spring constant.

Accordingly, the vibrating plate 41 is supported relative to the frame plate 61 in a flexible manner by the two connecting portions 62. Bending vibration of the vibrating plate is almost uninhibited as a result. In other words, a peripheral portion (and of course a central portion) of the piezoelectric actuator 40 is unrestricted or substantially unrestricted.

Note that the spacer 53A is provided in order to hold the piezoelectric actuator 40 at a set gap from the flexible plate 51. The frame plate 61 is provided with an external terminal 63 to achieve an electrical connection.

The vibrating plate 41, the frame plate 61, the connecting portions 62, and the external terminal 63 are formed preferably by carrying out a stamping process on a metal plate, for example, and the vibrating plate unit 60 is configured of those elements.

The spacer 53B, which is configured of a resin, is bonded and anchored to a top surface of the frame plate 61. The spacer 53B is as thick as or slightly thicker than the piezoelectric element 42. The frame plate 61 configures a portion of a pump housing 80. The electrode conducting plate 70 described hereinafter is electrically insulated from the vibrating plate unit 60.

The electrode conducting plate 70, which is configured of a metal, is bonded and anchored to a top surface of the spacer 53B. The electrode conducting plate 70 preferably includes a frame section 71 including a circular or substantially circular opening, an internal terminal 73 that projects into the opening, and an external terminal 72 that projects to the exterior.

A leading end of the internal terminal 73 is soldered to a surface of the piezoelectric element 42. The internal terminal 73 is prevented from vibrating by setting the solder location to a location corresponding to a node point of a bending vibration in the piezoelectric actuator 40.

The spacer 53C, which is configured of a resin, is bonded to and anchored upon the electrode conducting plate 70. Here, the spacer 53C preferably has the same or approximately the same thickness as the piezoelectric element 42. The spacer 53C is a spacer configured to ensure that the solder portion of the internal terminal 73 does not make contact with the cover plate 54 when the piezoelectric actuator 40 vibrates. The spacer 53C also prevents the surface of the piezoelectric element 42 from coming too close to the cover plate 54 and causing a drop in the vibration amplitude due to air resistance. Accordingly, it is preferable for the thickness of the spacer 53C to the same or approximately the same thickness as the piezoelectric element 42, as mentioned earlier.

Ejection holes 55 and 56 are provided in the cover plate 54. The cover plate 54 is placed on an upper portion of the spacer 53C and covers the periphery of the piezoelectric actuator 40.

Meanwhile, a suction hole 52 is provided in the center of the flexible plate 51. The spacer 53A, which adds approximately several tens of μm to the thickness of the reinforcement plate 43, is inserted between the flexible plate 51 and the vibrating plate unit 60. Accordingly, the vibrating plate 41 is not restricted by the frame plate 61 even if the spacer 53A is present, and thus the interval changes automatically in accordance with load fluctuations.

However, the vibrating plate 41 is slightly susceptible to restrictions from the connecting portions 62 (spring terminals), and thus inserting the spacer 53A in this manner makes it possible to purposefully secure a gap and increase the flow rate at times of low load. Furthermore, even in the case where the spacer 53A is inserted, the connecting portions 62 (spring terminals) bend and the gap between opposing regions of the piezoelectric actuator 40 and the flexible plate automatically shrinks at times of high load, which makes operations at high pressures possible.

Although the connecting portions 62 are provided in two locations in the example shown in FIG. 2, the connecting portions 62 may be provided in three or more locations. Although the connecting portions 62 do not interfere with the vibration of the piezoelectric actuator 40, the connecting portions 62 do slightly affect the vibration, and thus connecting (holding) the piezoelectric actuator 40 in three locations, for example, makes it possible to hold the actuator in a more natural manner and prevent the piezoelectric element 42 from breaking.

The substrate 91, in the center of which is provided a cylindrical or substantially cylindrical opening portion 92, is provided below the flexible plate 51. A portion of the flexible plate 51 is exposed by the opening portion 92 of the substrate 91. This circular or substantially circular exposed portion vibrates at substantially the same frequency as the piezoelectric actuator 40, due to pressure fluctuations produced when the piezoelectric actuator 40 vibrates.

The configuration of the flexible plate 51 and the substrate 91 produces a mobile portion that can bend and vibrate in the center or near the center of the region of the flexible plate 51 that opposes the piezoelectric actuator, and the peripheral portion then defines and serves as a fixed portion that is restricted or substantially restricted. A natural vibration frequency of this circular or substantially circular mobile portion is designed to be the same as or slightly lower than a driving frequency of the piezoelectric actuator 40.

Accordingly, when a driving voltage is applied to the external terminals 63 and 72, the piezoelectric actuator 40 bends and vibrates in a concentric circle shape, and the exposed portion of the flexible plate 51 centered on the suction hole 52 also vibrates at a high amplitude in response to the piezoelectric actuator 40 vibrating.

When a vibration phase of the flexible plate 51 is delayed relative to a vibration phase of the piezoelectric actuator 40 (by about 90°, for example), fluctuations in the thickness of the gap space between the flexible plate 51 and the piezoelectric actuator 40 substantially increase. The capabilities of the pump are further improved as a result.

Next, the structure of the valve 101 will be described in detail with reference to FIGS. 1 and 4-6.

Figure 4:
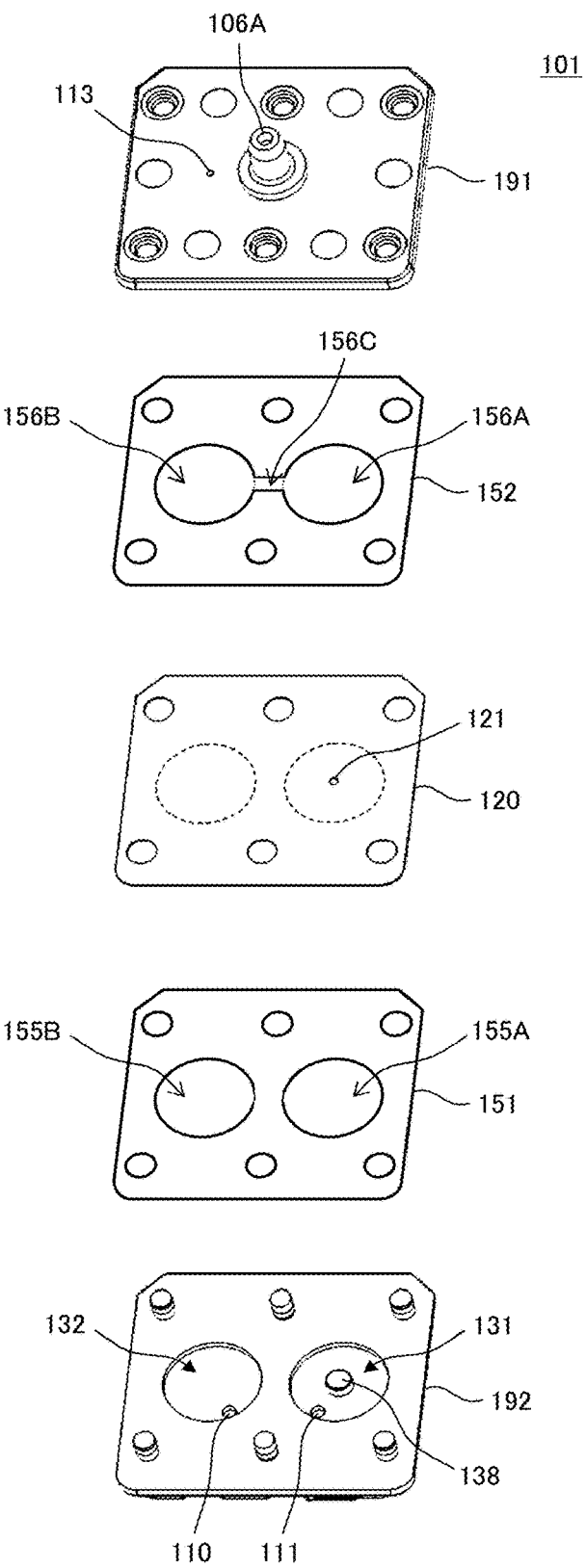
FIG. 4 is an exploded perspective view illustrating a valve 101 shown in FIG. 1.
Figure 5:
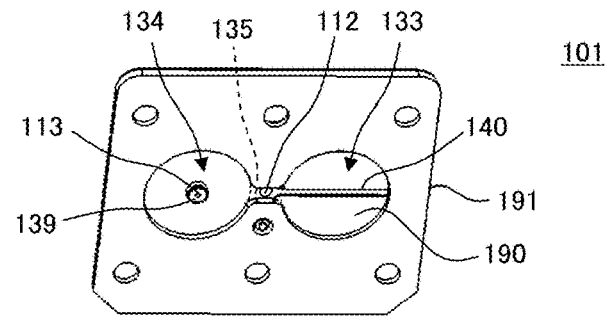
FIG. 5 is an exploded perspective view illustrating the valve 101 shown in FIG. 1.
Figure 5:
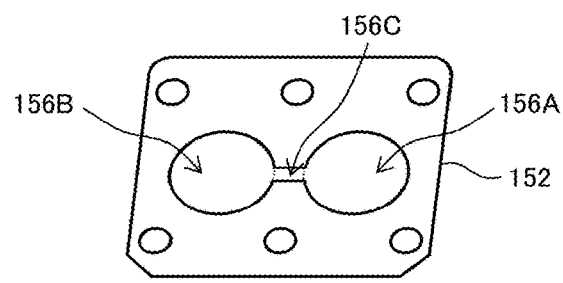
Figure 5:
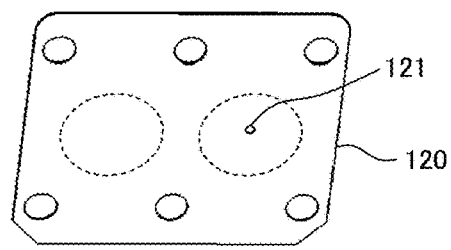
Figure 5:
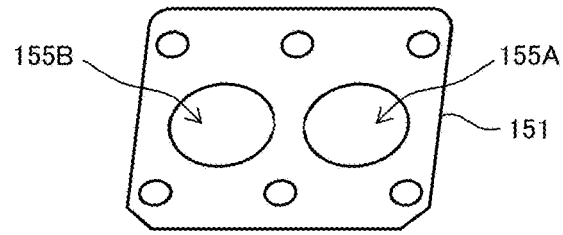
Figure 5:
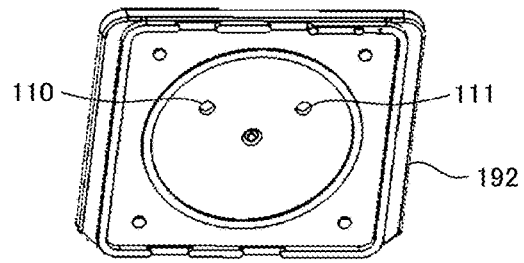
Figure 6:
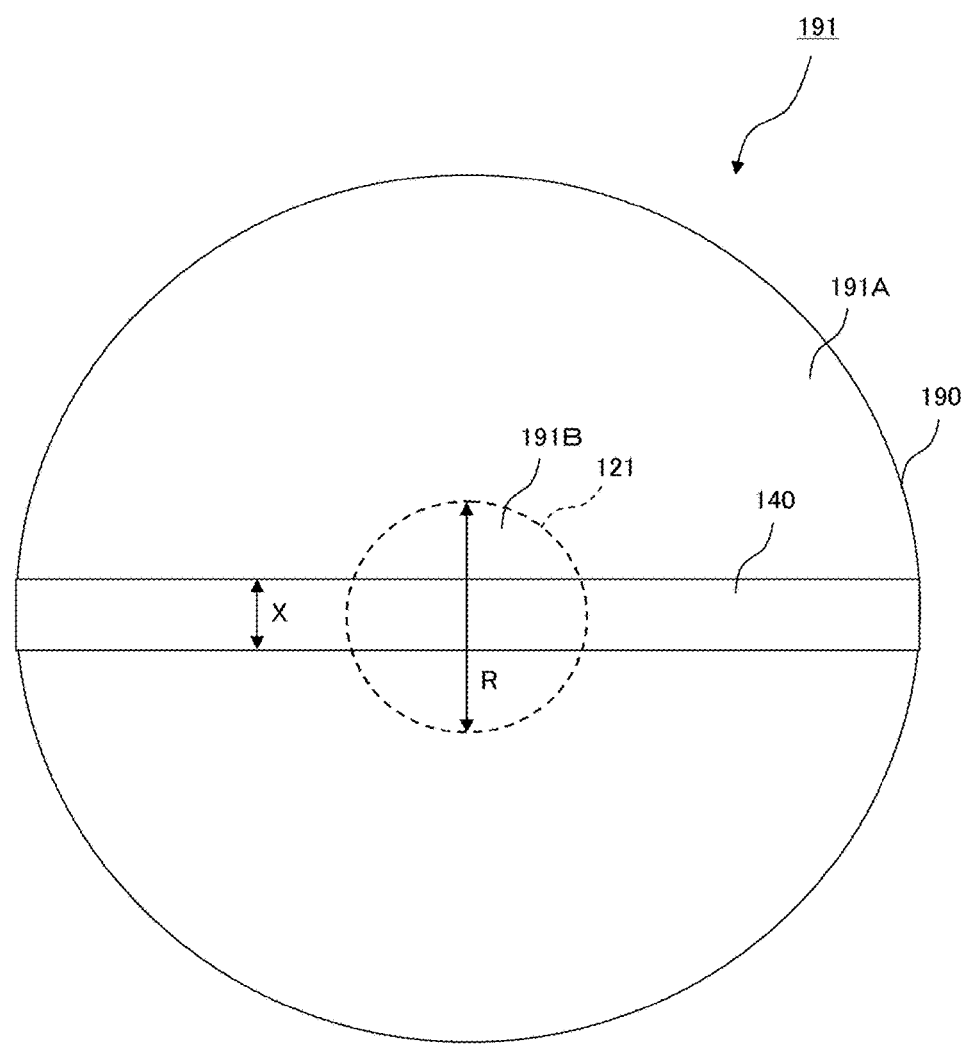
FIG. 6 is an enlarged front view illustrating the primary components of an upper valve housing 191 shown in FIG. 5.

FIGS. 4 and 5 are exploded perspective views illustrating the valve 101 shown in FIG. 1. FIG. 4 is an exploded perspective view of the valve 101 seen from the top surface side that is connected to the cuff 109, and FIG. 5 is an exploded perspective view of the valve 101 seen from the bottom surface side that is bonded to the piezoelectric pump 10. FIG. 6 is an enlarged front view illustrating the primary components of the upper valve housing 191 shown in FIG. 5.

Note that a "first opening portion" corresponds to a first ventilation hole 111. A "second opening portion" corresponds to a second ventilation hole 112. Furthermore, a "first valve chamber" corresponds to a first lower valve chamber 131. A "second valve chamber" corresponds to a first upper valve chamber 133.

As shown in FIGS. 1, 4, and 5, the valve 101 has a structure in which a lower valve housing 192, a first adhesive sheet 151 configured of a rectangular or substantially rectangular thin film, a diaphragm 120 configured of a rectangular or substantially rectangular thin film, a second adhesive sheet 152 configured of a rectangular or substantially rectangular thin film, and the upper valve housing 191 are stacked in that order. The upper valve housing 191 and the lower valve housing 192 configure a valve housing 130.

The lower valve housing 192 and the diaphragm 120 are bonded to each other by the first adhesive sheet 151, and the diaphragm 120 and the upper valve housing 191 are bonded to each other by the second adhesive sheet 152.

As shown in FIG. 1, the top surface of the piezoelectric pump 10 is bonded to a bottom surface of the lower valve housing 192. As shown in FIGS. 1, 4, and 5, a fourth ventilation hole 110 that communicates with the ejection hole 56 of the piezoelectric pump 10, the first ventilation hole 111 that communicates with the ejection hole 55 of the piezoelectric pump 10, and a cylindrical projecting portion 138 that projects toward the diaphragm 120 side are provided in the lower valve housing 192.

As shown in FIGS. 1, 4, and 5, the second ventilation hole 112 that communicates with the cuff 109, a third ventilation hole 113 that communicates with the exterior of the fluid control apparatus 100, and a valve seat 139 that projects toward the diaphragm 120 side from the periphery of the third ventilation hole 113 are provided in the upper valve housing 191. The valve seat 139 has a cylindrical or substantially cylindrical shape in a central area of which the third ventilation hole 113 is provided.

As shown in FIGS. 1, 4, and 5, a circular or substantially circular hole portion 121 is provided in a central portion of a region of the diaphragm 120 that opposes the projecting portion 138. The diameter of the hole portion 121 is set to be smaller than the diameter of a face of the projecting portion 138 that makes contact with the diaphragm 120.

The diaphragm 120 is sandwiched from both sides between the upper valve housing 191 and the lower valve housing 192, and is bonded to the upper valve housing 191 and the lower valve housing 192 so as to make contact with the valve seat 139 and so that the periphery of the hole portion 121 makes contact with the projecting portion 138.

The diaphragm 120 divides the interior of the valve housing 130 as a result. The ring-shaped first lower valve chamber 131 that communicates with the first ventilation hole 111, a cylindrical or substantially cylindrical second lower valve chamber 132 that communicates with the fourth ventilation hole 110, the cylindrical or substantially cylindrical first upper valve chamber 133 that communicates with the second ventilation hole 112 via a communication channel 135, and a ring-shaped second upper valve chamber 134 that communicates with the first upper valve chamber 133 via the communication channel 135 are configured as well. The shapes of the valve chambers mentioned here are shapes as viewed from above, in a direction perpendicular or substantially perpendicular to the diaphragm 120.

The diameters of the first lower valve chamber 131, the second lower valve chamber 132, the first upper valve chamber 133, and the second upper valve chamber 134 are each preferably about 7.0 mm, for example. The diameter of the face of the projecting portion 138 that makes contact with the diaphragm 120 is preferably about 1.5 mm, for example.

First through-holes 155A-155C are provided in a region of the first adhesive sheet 151 that faces the first lower valve chamber 131 and the second lower valve chamber 132. The first through-hole 155A has a circular or substantially circular shape that has approximately the same center axis as the first lower valve chamber 131, for example. The first through-hole 155B has a circular or substantially circular shape that has approximately the same center axis as the second lower valve chamber 132, for example. The first through-holes 155A and 155B preferably each have a diameter of about 6.6 mm, for example.

Accordingly, the diameter of the first through-hole 155A is greater than the diameter of the projecting portion 138 and smaller than the diameter of the first lower valve chamber 131. In other words, an outer circumference of the first through-hole 155A is greater than an outer circumference of the projecting portion 138 and smaller than an outer circumference of the first lower valve chamber 131.

Likewise, the diameter of the first through-hole 155B is smaller than the diameter of the second lower valve chamber 132. In other words, the outer circumference of the first through-hole 155B is smaller than the outer circumference of the second lower valve chamber 132.

Second through-holes 156A-156C are provided in a region of the second adhesive sheet 152 that faces the first upper valve chamber 133, the communication channel 135, and the second upper valve chamber 134. The second through-hole 156A has a circular or substantially circular shape that has approximately the same center axis as the first upper valve chamber 133, for example. The second through-hole 156B has a circular or substantially circular shape that has approximately the same center axis as the second upper valve chamber 134, for example. The second through-holes 156A and 156B each have a diameter preferably of about 6.6 mm, for example.

Accordingly, the diameter of the second through-hole 156A is smaller than the diameter of the first upper valve chamber 133. In other words, the outer circumference of the second through-hole 156A is smaller than the outer circumference of the first upper valve chamber 133.

Likewise, the diameter of the second through-hole 156B is smaller than the diameter of the second upper valve chamber 134. In other words, the outer circumference of the second through-hole 156B is smaller than the outer circumference of the second upper valve chamber 134.

As described thus far, according to the valve 101, a portion of the first adhesive sheet 151 is located within the first lower valve chamber 131 and the second lower valve chamber 132. Likewise, a portion of the second adhesive sheet 152 is located within the first upper valve chamber 133 and the second upper valve chamber 134.

Meanwhile, as shown in FIG. 6, the upper valve housing 191 includes, in the first upper valve chamber 133, a wall portion 190 that opposes the diaphragm 120. The wall portion 190 includes a region 191A that opposes an area of the diaphragm 120 aside from the hole portion 121 and a region 191B that opposes the hole portion 121 in the diaphragm 120.

A groove 140 is provided in the wall portion 190 of the upper valve housing 191 that opposes the diaphragm 120 in the first upper valve chamber 133. The groove 140 is a groove that allows the first lower valve chamber 131 and the first upper valve chamber 133 to communicate via the hole portion 121 when the diaphragm 120 makes contact with the wall portion 190. Note that the groove 140 corresponds to a "flow channel formation portion".

A width X of the groove 140 is, as shown in FIG. 6, shorter than a diameter R of the region 191B of the upper valve housing 191 that opposes the hole portion 121 of the diaphragm 120 in the first upper valve chamber 133. Meanwhile, as shown in FIGS. 1, 5, and 6, the groove 140 is arranged to encompass a range from the region 191B to the second ventilation hole 112 of the upper valve housing 191. The groove 140 is arranged so as to extend from the region 191B to the region 191A of the upper valve housing 191.

The projecting portion 138 is arranged in the lower valve housing 192 so as to pressurize the periphery of the hole portion 121 in the diaphragm 120.

Accordingly, the valve 101 includes a check valve 102 and an exhaust valve 103, as shown in FIG. 1.

First, the check valve 102 is configured by a portion of the lower valve housing 192 that includes the first ventilation hole 111, a portion of the upper valve housing 191 that includes the second ventilation hole 112, the periphery of the hole portion 121 in the diaphragm 120, and the projecting portion 138 that makes contact with that periphery and covers the hole portion 121. The check valve 102 allows the fluid to flow from the first lower valve chamber 131 side toward the first upper valve chamber 133 side and blocks the fluid from flowing from the first upper valve chamber 133 side toward the first lower valve chamber 131 side.

As a result of a pressure difference between the first lower valve chamber 131 and the first upper valve chamber 133, the check valve 102 causes the diaphragm 120 to come into contact with or separate from the projecting portion 138.

Next, the exhaust valve 103 is configured by a portion of the lower valve housing 192 that includes the fourth ventilation hole 110, a portion of the upper valve housing 191 that includes the second ventilation hole 112 and the third ventilation hole 113, a portion of the diaphragm 120, and the valve seat 139 that projects toward the diaphragm 120 side from the periphery of the third ventilation hole 113, makes contact with the diaphragm 120, and is covered thereby.

As a result of a pressure difference between the second lower valve chamber 132 and the second upper valve chamber 134, the exhaust valve 103 causes the diaphragm 120 to come into contact with or separate from the valve seat 139.

Next, operations of the fluid control apparatus 100 during blood pressure measurement will be described.

Figure 7:
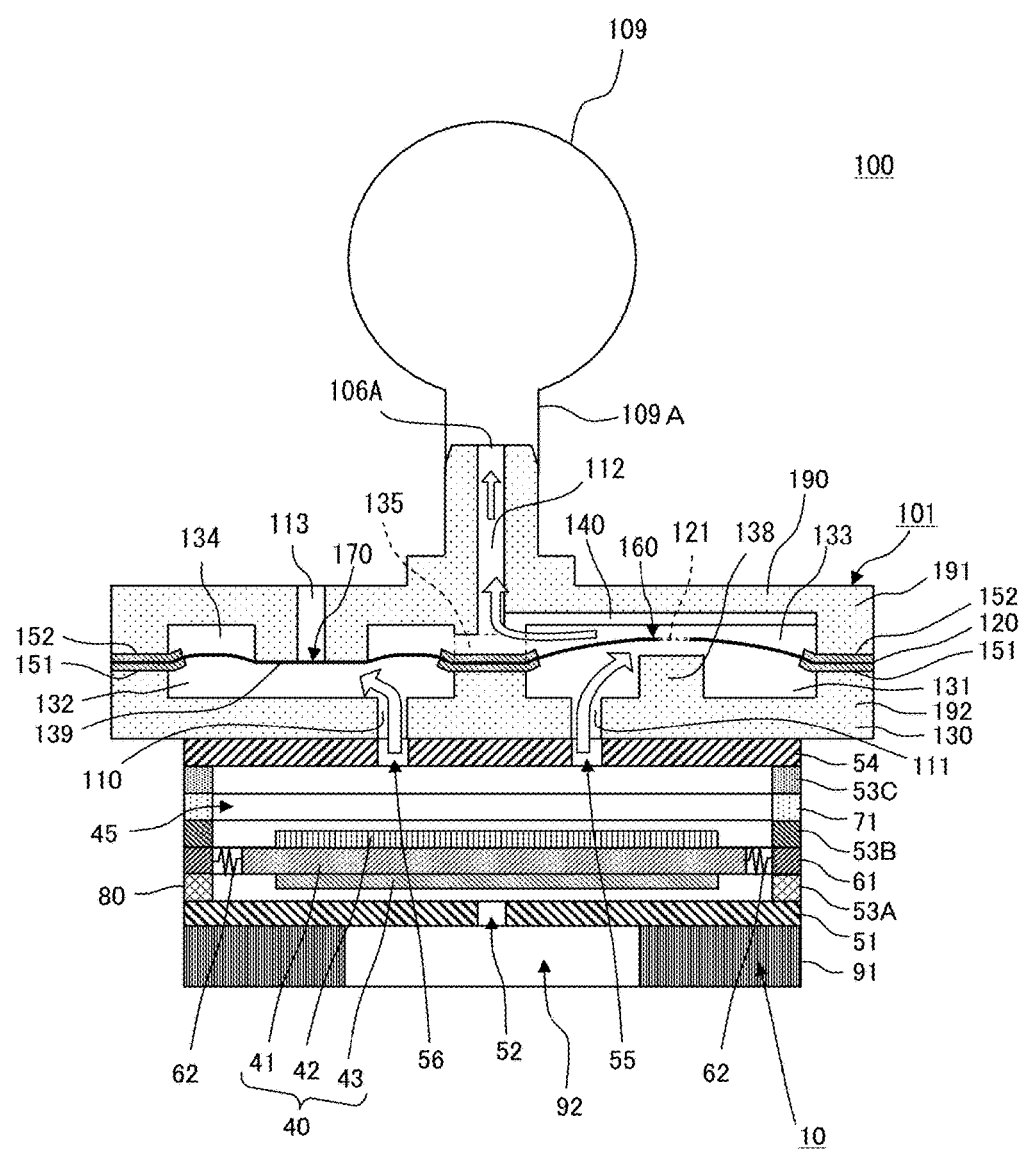
FIG. 7 is a schematic diagram illustrating the flow of air in the fluid control apparatus 100 shown in FIG. 1 when the piezoelectric pump 10 is driven.

FIG. 7 is a schematic diagram illustrating the flow of air in the fluid control apparatus 100 shown in FIG. 1 when the piezoelectric pump 10 is driven.

When blood pressure measurement begins, first, the fluid control apparatus 100 drives the piezoelectric pump 10. When the piezoelectric pump 10 is driven, first, air flows from the opening portion 92 and the suction hole 52 into a pump chamber 45 within the piezoelectric pump 10. Next, the air is ejected from the ejection holes 55 and 56, and flows into both the second lower valve chamber 132 and the first lower valve chamber 131 of the valve 101.

Figure 8:
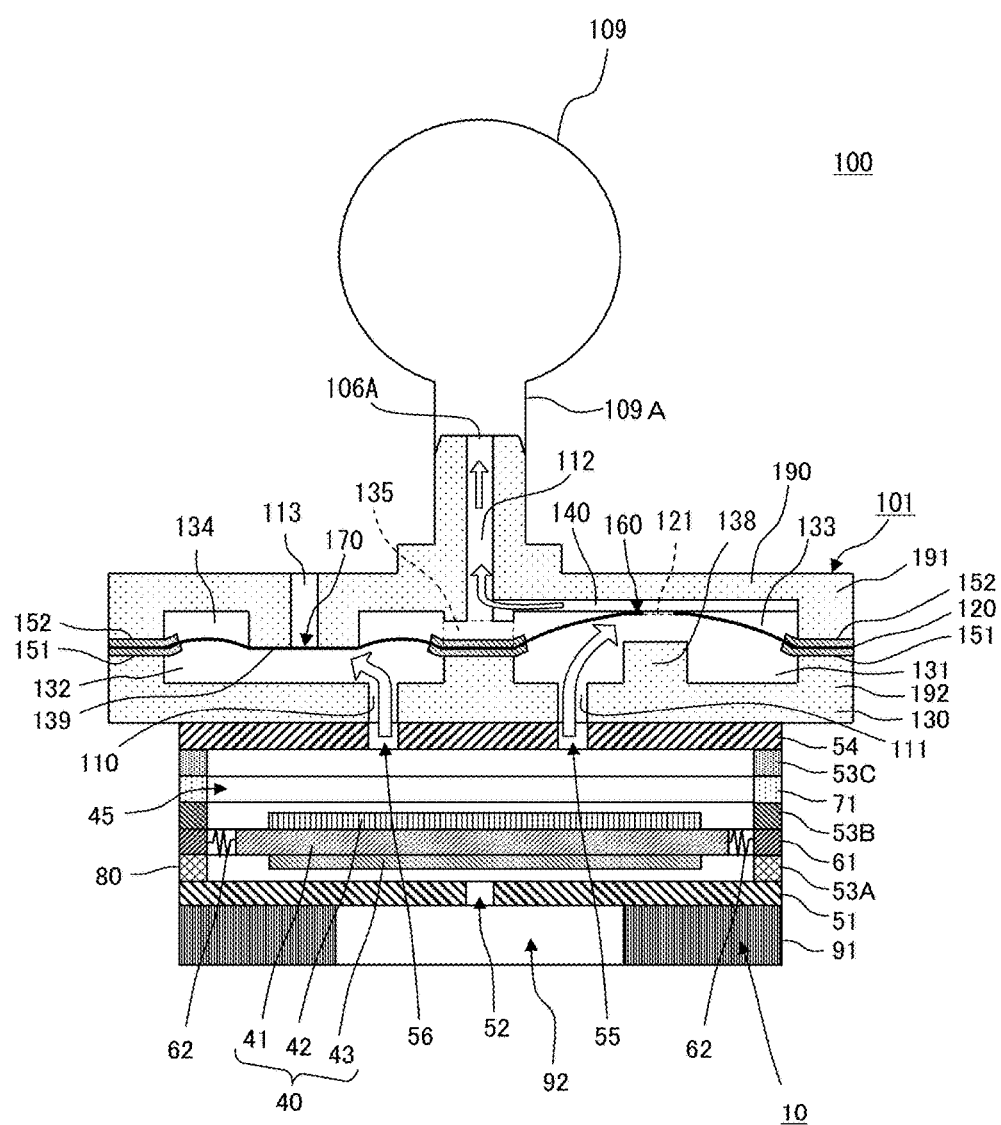
FIG. 8 is a schematic diagram illustrating the flow of air in the fluid control apparatus 100 shown in FIG. 1 when the piezoelectric pump 10 is driven and an ejection pressure of the piezoelectric pump 10 has risen suddenly.

As a result, in the exhaust valve 103, a pressure in the second lower valve chamber 132 becomes higher than a pressure in the second upper valve chamber 134. Accordingly, as shown in FIG. 8, the diaphragm 120 seals the third ventilation hole 113 and blocks the passage of air between the second ventilation hole 112 and the third ventilation hole 113.

Meanwhile, in the check valve 102, a pressure in the first lower valve chamber 131 becomes higher than a pressure in the first upper valve chamber 133. Accordingly, the periphery of the hole portion 121 in the diaphragm 120 separates from the projecting portion 138, and the first ventilation hole 111 and the second ventilation hole 112 communicate via the hole portion 121.

As a result, the air is discharged from the piezoelectric pump 10, through the first ventilation hole 111, the hole portion 121, and the second ventilation hole 112 of the valve 101, and to the cuff 109 (see FIG. 7), and the pressure (air pressure) within the cuff 109 increases.

Note that the diaphragm 120 is anchored to the valve housing 130 so that the periphery of the hole portion 121 in the diaphragm 120 makes contact with the projecting portion 138. The projecting portion 138 pressurizes the periphery of the hole portion 121 in the diaphragm 120.

Accordingly, the air that flows out from the hole portion 121 via the first ventilation hole 111 in the valve 101 takes on a slightly lower pressure than the ejection pressure of the piezoelectric pump 10, and flows into the first upper valve chamber 133 and the second upper valve chamber 134 from the hole portion 121. On the other hand, the ejection pressure of the piezoelectric pump 10 acts on the second lower valve chamber 132.

As a result, in the valve 101, the pressure in the second lower valve chamber 132 slightly exceeds the pressure in the second upper valve chamber 134, the diaphragm 120 seals the third ventilation hole 113, and the hole portion 121 remains in an open state.

FIG. 8 is a schematic diagram illustrating the flow of air in the fluid control apparatus 100 when the piezoelectric pump 10 shown in FIG. 7 is driven and the ejection pressure of the piezoelectric pump 10 has risen suddenly.

Here, when the pressure in the first lower valve chamber 131 suddenly rises, the diaphragm 120 deforms greatly, and there are cases where the periphery of the hole portion 121 in the diaphragm 120 separates greatly from the projecting portion 138, as shown in FIG. 8.

In this case, according to this configuration, the diaphragm 120 makes contact with the region 191A of the upper valve housing 191 (see FIG. 6), but the hole portion 121 in the diaphragm 120 communicates with the first upper valve chamber 133 via the groove 140.

Accordingly, with the check valve 102 provided with the groove 140, even if, the pressure in the first lower valve chamber 131 has risen suddenly, the hole portion 121 in the diaphragm 120 will not be covered, and the air will flow from the first lower valve chamber 131 into the first upper valve chamber 133 via the hole portion 121. In other words, a flow channel for the air is secured.

Therefore, according to the check valve 102, the transport of air is prevented from being stopped even in the case where the ejection pressure of the piezoelectric pump 10 has risen suddenly.

Furthermore, in the check valve 102, the width X of the groove 140 is shorter than the diameter R of the hole portion 121 in the diaphragm 120 (see FIG. 6). Therefore, according to the check valve 102, the periphery of the hole portion 121 in the diaphragm 120 is prevented from making contact with the groove 140, which in turn prevents the hole portion 121 from being covered. Accordingly, the transport of air is further suppressed or prevented from stopping.

Meanwhile, in the upper valve housing 191 of the check valve 102, the groove 140 is provided in a range spanning from the region 191B that opposes the hole portion 121 in the diaphragm 120 to the second ventilation hole 112 (see FIG. 6).

Accordingly, even if the pressure in the first lower valve chamber 131 becomes much higher than the pressure in the first upper valve chamber 133 and the diaphragm 120 makes contact with a wide range of the upper valve housing 191 as a result, the hole portion 121 in the diaphragm 120 communicates with the first upper valve chamber 133 via the groove 140.

As a result, the hole portion 121 in the diaphragm 120 will not be covered, and the air will flow from the first lower valve chamber 131 into the first upper valve chamber 133 through the hole portion 121. In other words, a flow channel for the air is secured. Accordingly, the transport of air is further suppressed or prevented from stopping.

Furthermore, according to this configuration, an air flow channel is secured even if the distance between the diaphragm 120 and the wall portion 190 of the upper valve housing 191 is significantly reduced, and thus the profile of the check valve 102 is significantly reduced as well.

Further still, as shown in FIGS. 4 and 5, in the valve 101, the valve chambers 131, 132, 133, and 134 each have circular or substantially circular outer shapes, and thus uniform tension acts on the diaphragm 120 (and particularly in the periphery near the hole portion 121).

Accordingly, the diaphragm 120 is suppressed or prevented from making contact with the hole portion 121 thereof tilted relative to the projecting portion 138, the hole portion 121 in the diaphragm 120 is suppressed from shifting relative to the projecting portion 138 in the horizontal direction, and so on. Therefore, according to the valve 101, the opening/closing of the respective valves is carried out with more certainty.

Figure 9:
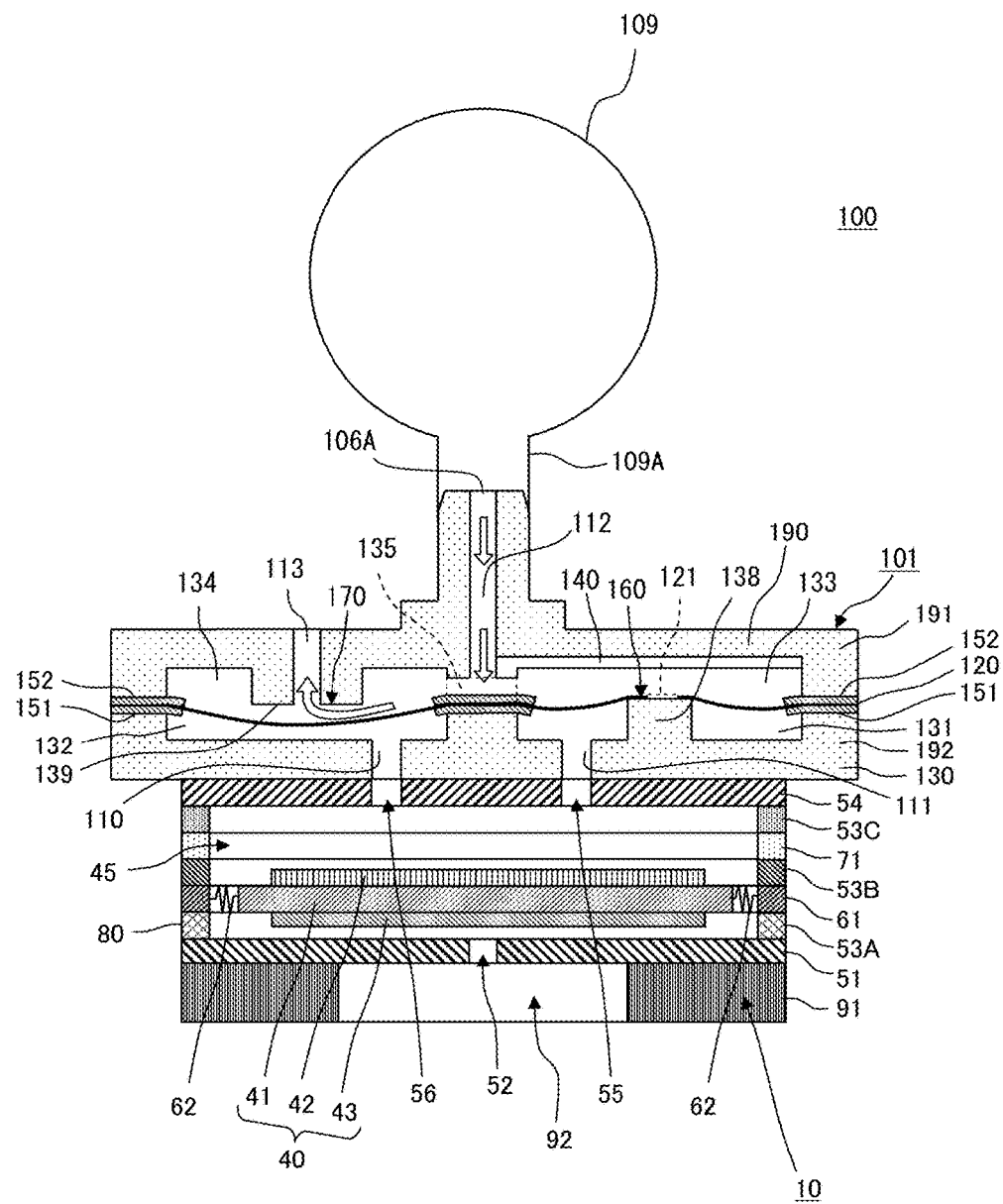
FIG. 9 is a schematic diagram illustrating the flow of air in the fluid control apparatus 100 shown in FIG. 1 immediately after driving of the piezoelectric pump 10 is stopped.

FIG. 9 is a schematic diagram illustrating the flow of air in the fluid control apparatus 100 shown in FIG. 1 immediately after the driving of the piezoelectric pump 10 has stopped.

When the blood pressure measurement ends, the fluid control apparatus 100 stops driving the piezoelectric pump 10. Here, when the driving of the piezoelectric pump 10 stops, the air in the pump chamber 45, the first lower valve chamber 131, and the second lower valve chamber 132 is quickly exhausted to the exterior of the fluid control apparatus 100 from the suction hole 52 and the opening portion 92 in the piezoelectric pump 10. Meanwhile, pressure from the cuff 109 acts on the first upper valve chamber 133 and the second upper valve chamber 134 from the second ventilation hole 112.

As a result, in the check valve 102, the pressure in the first lower valve chamber 131 becomes lower than the pressure in the first upper valve chamber 133. The diaphragm 120 makes contact with the projecting portion 138 and seals the hole portion 121.

Meanwhile, in the exhaust valve 103, the pressure in the second lower valve chamber 132 becomes lower than the pressure in the second upper valve chamber 134. The diaphragm 120 separates from the valve seat 139 and opens the third ventilation hole 113.

In other words, in the valve 101, the second ventilation hole 112 and the third ventilation hole 113 communicate via the communication channel 135 and the second upper valve chamber 134. Through this, the air in the cuff 109 is quickly exhausted from the third ventilation hole 113 via the second ventilation hole 112, the communication channel 135, and the second upper valve chamber 134 (see FIG. 9).

Therefore, according to the valve 101 in this preferred embodiment, air is quickly exhausted from the cuff 109 after the cuff 109 has been filled with compressed air.

Meanwhile, in the valve 101, part of the first adhesive sheet 151 is located within the first lower valve chamber 131 and the second lower valve chamber 132, and a portion of the second adhesive sheet 152 is located within the first upper valve chamber 133 and the second upper valve chamber 134, as described earlier.

Accordingly, the first adhesive sheet 151 and the second adhesive sheet 152 bond the valve housing 130 and the diaphragm 120, and foreign objects present in the valve chambers 131, 132, 133, and 134 are caught.

Therefore, according to the valve 101, even if foreign objects have entered into the valve 101, for example, erroneous operations caused by such foreign objects are suppressed or prevented. In particular, the third ventilation hole 113 of the valve seat 139 in the exhaust valve 103 is suppressed or prevented from being blocked by foreign objects.

The fluid control apparatus 100 that includes the valve 101 according to this preferred embodiment achieves the same effects as those described thus far.

Second Preferred Embodiment

A fluid control apparatus 200 according to a second preferred embodiment of the present invention will be described hereinafter.

Figure 10:
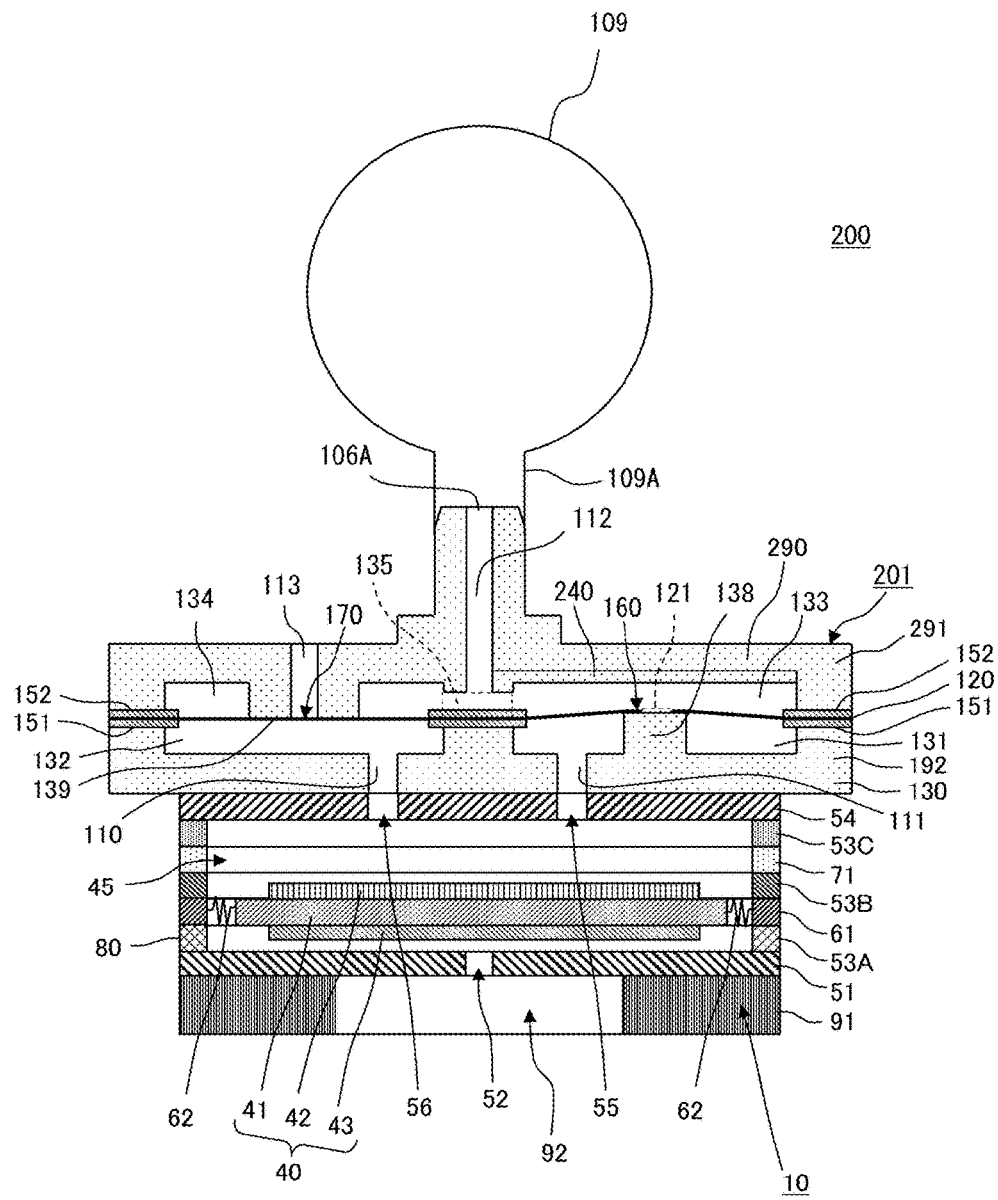
FIG. 10 is a cross-sectional view illustrating the primary components of a fluid control apparatus 200 according to a second preferred embodiment of the present invention.
Figure 11:
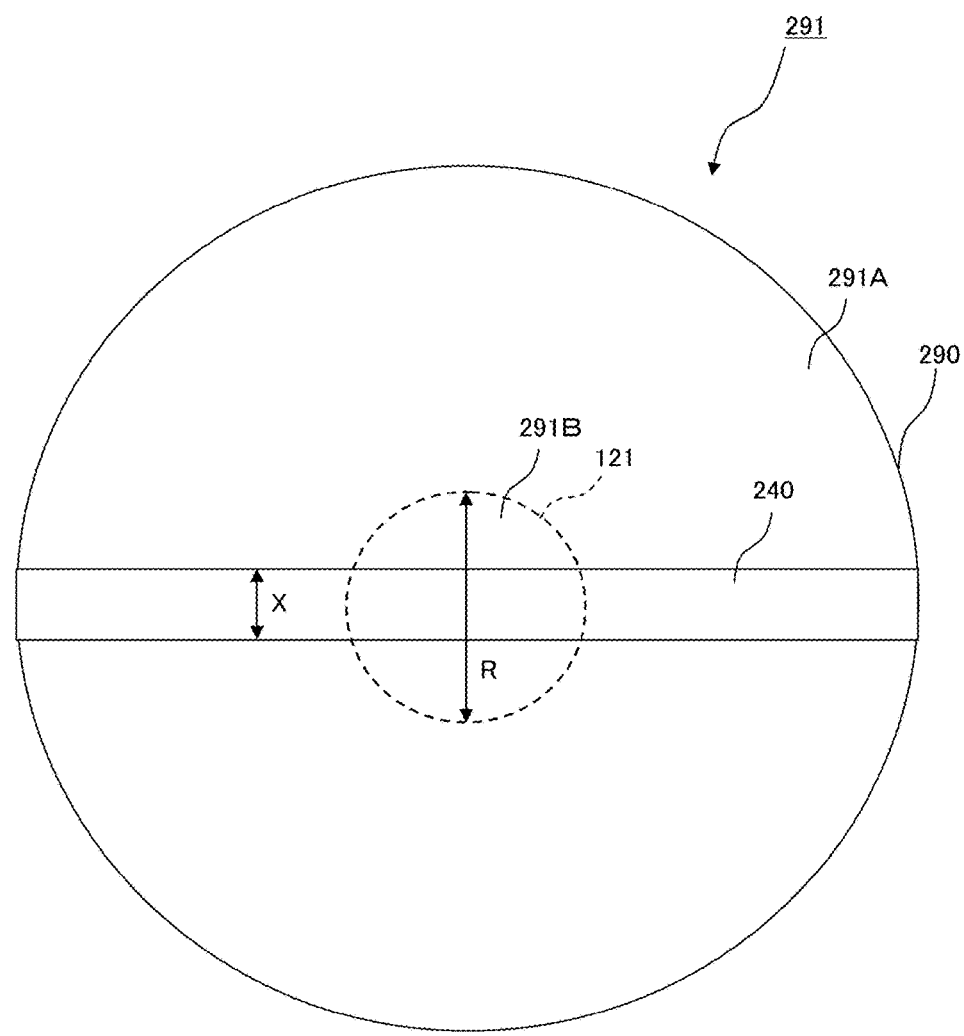
FIG. 11 is an enlarged front view illustrating the primary components of an upper valve housing 291 shown in FIG. 10.
Figure 12:
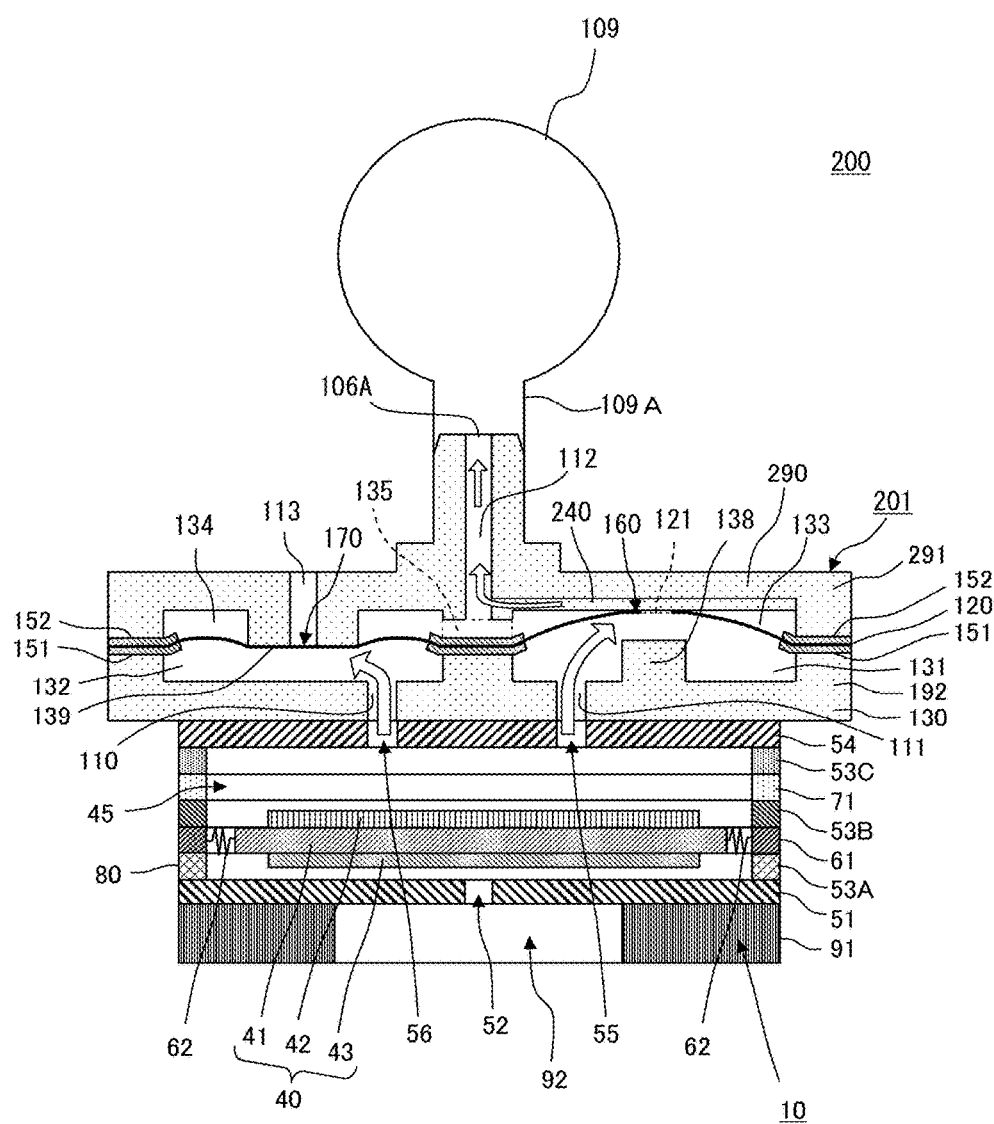
FIG. 12 is a schematic diagram illustrating the flow of air in the fluid control apparatus 200 shown in FIG. 10 when the piezoelectric pump 10 is driven and an ejection pressure of the piezoelectric pump 10 has risen suddenly.

FIG. 10 is a cross-sectional view illustrating the primary components of the fluid control apparatus 200 according to the second preferred embodiment of the present invention. FIG. 11 is an enlarged front view illustrating the primary components of an upper valve housing 291 shown in FIG. 10. FIG. 12 is a schematic diagram illustrating the flow of air in the fluid control apparatus 200 when the piezoelectric pump 10 is driven and the ejection pressure of the piezoelectric pump 10 has risen suddenly while the fluid control apparatus 200 shown in FIG. 10 is operating.

The fluid control apparatus 200 differs from the fluid control apparatus 100 in that the upper valve housing 291 of a valve 201 includes a projection 240 instead of the groove 140. Note that the projection 240 corresponds to a "flow channel formation portion". The other elements of the configuration are the same.

To describe in detail, the upper valve housing 291 includes, in the first upper valve chamber 133, a wall portion 290 that opposes the diaphragm 120. The wall portion 290 includes a region 291A that opposes an area of the diaphragm 120 aside from the hole portion 121 and a region 291B that opposes the hole portion 121 in the diaphragm 120.

To describe in further detail, the projection 240 is provided in the wall portion 290 of the upper valve housing 291 that opposes the diaphragm 120 in the first upper valve chamber 133. The projection 240 is a projection that allows the first lower valve chamber 131 and the first upper valve chamber 133 to communicate via the hole portion 121 when the diaphragm 120 makes contact with the wall portion 290 of the upper valve housing 291.

A width X of the projection 240 is, as shown in FIG. 11, shorter than a diameter R of the region 291B of the upper valve housing 291 that opposes the hole portion 121 of the diaphragm 120 in the first upper valve chamber 133. The projection 240 is arranged so as to extend from the region 291B to the region 291A of the upper valve housing 291.

In the valve 201 according to this preferred embodiment as well, when the pressure in the first lower valve chamber 131 suddenly rises, the diaphragm 120 deforms greatly, and there are cases where the periphery of the hole portion 121 in the diaphragm 120 separates by a significant amount from the projecting portion 138, as shown in FIG. 12.

In such a case, with the valve 201, the diaphragm 120 makes contact with the projection 240, a gap is defined between the diaphragm 120 and the region 291A of the upper valve housing 291, and the hole portion 121 in the diaphragm 120 communicates with the first upper valve chamber 133.

Accordingly, with the valve 201 provided with the projection 240, even if, the pressure in the first lower valve chamber 131 has risen suddenly, the hole portion 121 in the diaphragm 120 will not be covered, and the air will flow from the first lower valve chamber 131 into the first upper valve chamber 133 via the hole portion 121. In other words, a flow channel for the air is secured.

Accordingly, the valve 201 and the fluid control apparatus 200 provide the same effects as those of the valve 101 and the fluid control apparatus 100 according to the first preferred embodiment.

Other Preferred Embodiments

Although the aforementioned preferred embodiments describe air as a fluid, it should be noted that the fluid is not limited thereto, and preferred embodiments of the present invention are applicable even when the fluid is a gas aside from air, a liquid, or the like.

In addition, although the aforementioned preferred embodiments describe providing a unimorph actuator that preferably bends and vibrates, a bimorph configuration in which piezoelectric elements are affixed to both sides of a vibrating plate and the plate bends and vibrates as a result may be used.

In addition, although the pump in the aforementioned preferred embodiments includes the actuator 40 that preferably bends and vibrates as a result of the piezoelectric element 42 extending and contracting, the present invention is not limited thereto. For example, an actuator that bends and vibrates through electromagnetic driving may be used instead.

In addition, although the aforementioned preferred embodiments describe the piezoelectric element as being configured preferably of a PZT-based ceramic material, the present invention is not limited thereto. The piezoelectric element may be configured of a non-leaded piezoelectric ceramic material such as a potassium sodium niobate-based ceramic material, an alkali niobate-based ceramic material, or the like.

In addition, although the aforementioned preferred embodiments describe the groove 140 or the projection 240 as preferably having an elongated, narrow shape as indicated in FIG. 6 or FIG. 11, the present invention is not limited thereto. The groove 140 or the projection 240 may have a cross shape, a polygon shape, an oval shape, or the like, for example.

In addition, although the aforementioned preferred embodiments describe there preferably being only a single groove 140 or projection 240, the present invention is not limited thereto. For example, a plurality of grooves 140 may be provided in the region 191A of the upper valve housing 191 shown in FIG. 6, and a plurality of projections 240 may be provided in the region 291A of the upper valve housing 291 shown in FIG. 11.

Figure 13:
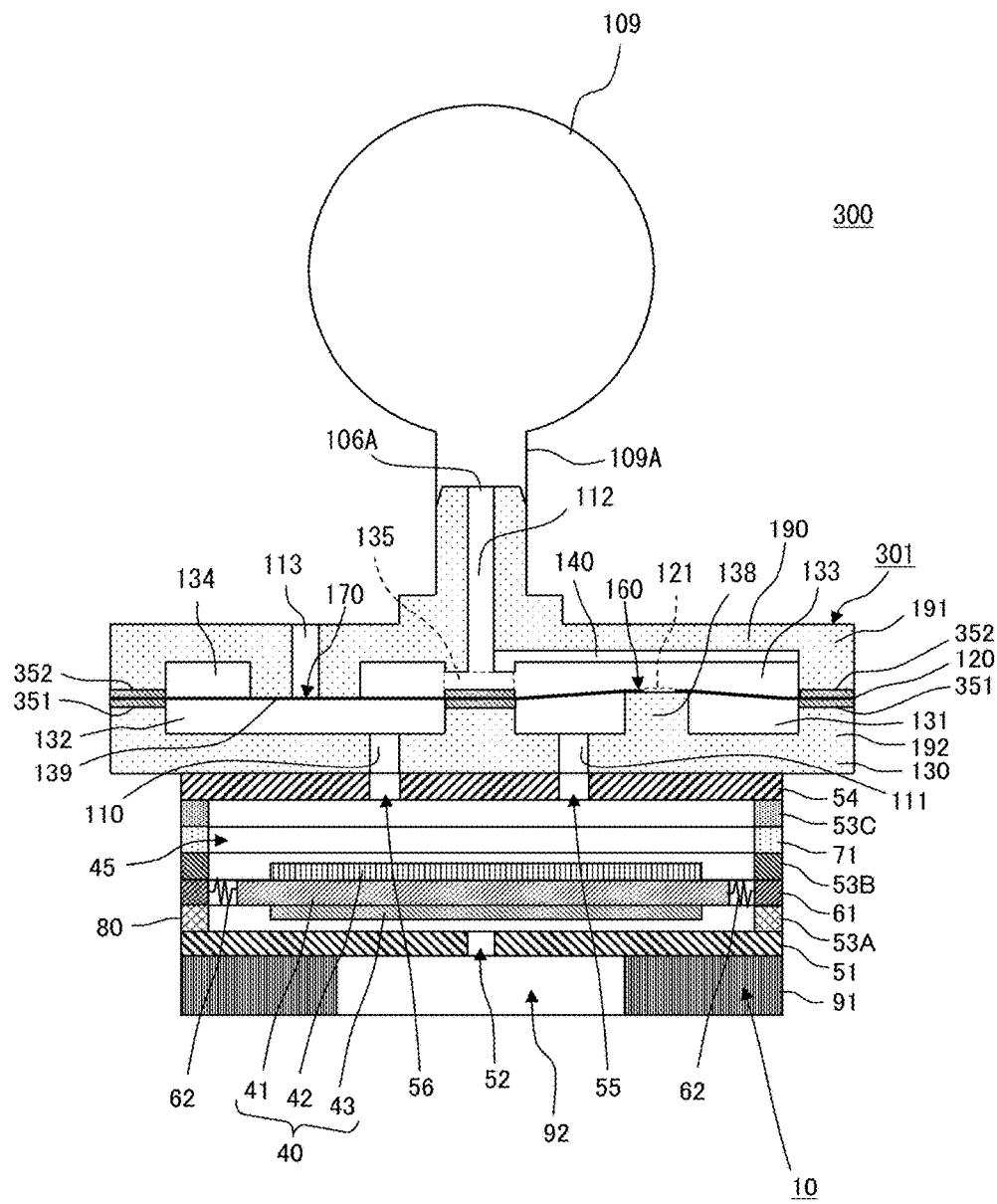
FIG. 13 is a cross-sectional view illustrating the primary components of a fluid control apparatus 300 according to a variation of the first preferred embodiment of the present invention.
Figure 14:
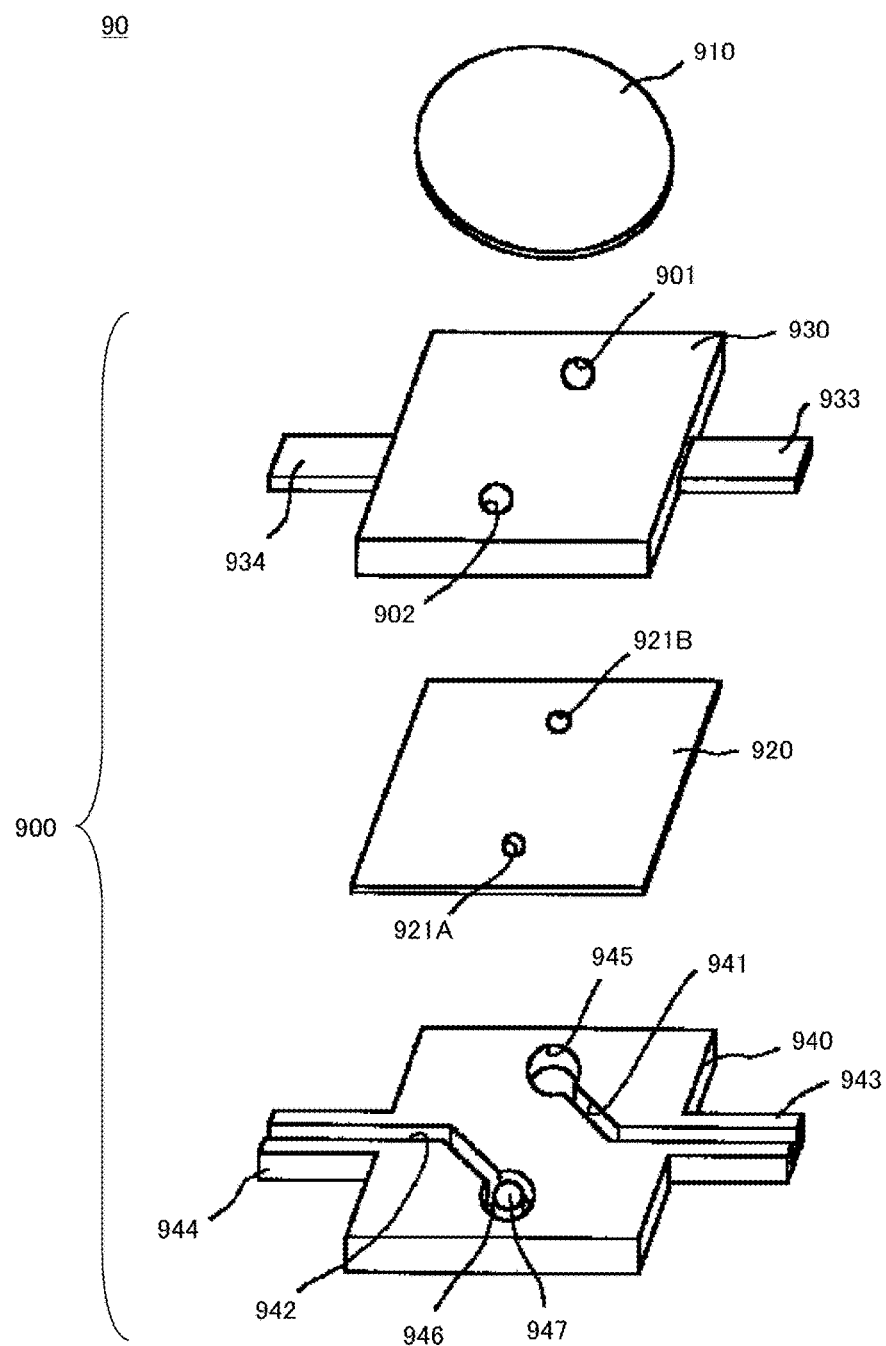
FIG. 14 is an exploded perspective view illustrating a diaphragm pump 90 according to Japanese Unexamined Patent Application Publication No. 2002-106469.
Figure 15:
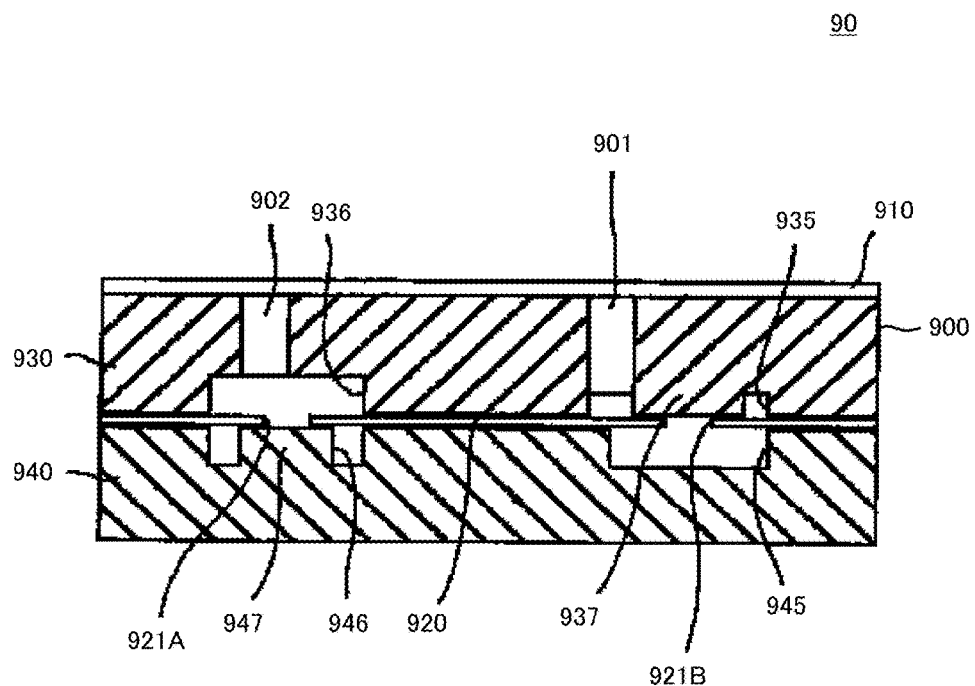
FIG. 15 is a cross-sectional view illustrating the primary components of the diaphragm pump 90 shown in FIG. 14.

In addition, although the valves 101 and 201 in the aforementioned preferred embodiments (see FIGS. 1 and 10) are described as preferably having the first adhesive sheet 151 in which the outer circumference of the first through-hole 155A is smaller than the outer circumference of the first lower valve chamber 131 and the outer circumference of the first through-hole 155B is smaller than the outer circumference of the second lower valve chamber 132, the present invention is not limited thereto. For example, a valve 301, shown in FIG. 13, may have a first adhesive sheet 351, in which the outer circumference of the first through-hole 155A is equal to the outer circumference of the first lower valve chamber 131 and the outer circumference of the first through-hole 155B is equal to the outer circumference of the second lower valve chamber 132.

Likewise, although the valves 101 and 201 in the aforementioned preferred embodiments (see FIGS. 1 and 10) are described as preferably having the second adhesive sheet 152 in which the outer circumference of the second through-hole 156A is smaller than the outer circumference of the first upper valve chamber 133 and the outer circumference of the second through-hole 156B is smaller than the outer circumference of the second upper valve chamber 134, the present invention is not limited thereto. For example, the valve 301, shown in FIG. 13, may have a second adhesive sheet 352, in which the outer circumference of the second through-hole 156A is equal to the outer circumference of the first upper valve chamber 133 and the outer circumference of the second through-hole 156B is equal to the outer circumference of the second upper valve chamber 134.

Finally, the aforementioned preferred embodiments are to be understood in all ways as exemplary and in no ways limiting. The scope of the present invention is defined not by the above preferred embodiments but by the scope of the appended claims. Furthermore, the scope of the present invention is intended to include all modifications within the scope and meaning equivalent to the scope of the appended claims.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A fluid control apparatus comprising:
   a pump including:
      a cover plate including an ejection hole;
      a piezoelectric actuator including a vibrating plate, a piezoelectric element, and a reinforcement plate;
      a flexible plate including a suction hole; and
      a substrate including an opening portion; wherein the cover plate, the piezoelectric actuator, the flexible plate, and the substrate are sequentially stacked; and when the pump is driven, a fluid flows from the opening portion and the suction hole into a gap between the piezoelectric actuator and the flexible plate in the pump and is ejected from the ejection hole; and a valve including:
 a lower valve housing including a ventilation hole and a lower valve chamber;
 an upper valve housing including an upper valve chamber; and
 a diaphragm allowing the lower valve chamber and the upper valve chamber to communicate with each other; wherein
 the lower valve housing, the diaphragm, and the upper valve housing are sequentially stacked;
the pump and the valve are bonded to each other so that the ventilation hole and the ejection hole communicate with each other; and
after the fluid ejected from the pump has flowed into the valve, in a case in which a pressure in the lower valve chamber is higher than a pressure in the upper valve chamber, the diaphragm allows the lower valve chamber and the upper valve chamber to communicate with each other.

2. The fluid control apparatus according to claim 1, wherein
 the lower valve chamber includes two lower valve chambers; and
 the upper valve chamber includes two upper valve chambers.

3. The fluid control apparatus according to claim 1, wherein the ejection hole includes two ejection holes.

4. The fluid control apparatus according to claim 1, wherein the diaphragm is provided with a hole portion.

5. The fluid control apparatus according to claim 4, wherein
 a flow channel formation portion is provided in a wall portion of the upper valve housing that opposes the diaphragm in the upper valve chamber; and
 the flow channel formation portion defines a flow channel connecting the upper valve chamber and the lower valve chamber when a periphery of the hole portion in the diaphragm makes contact with the wall portion.

6. The fluid control apparatus according to claim 5, wherein the flow channel formation portion is a groove.

7. The fluid control apparatus according to claim 5, wherein the flow channel formation portion is a projection.

8. The fluid control apparatus according to claim 5, wherein a width of the flow channel formation portion is smaller than a diameter of the hole portion.

9. The fluid control apparatus according to claim 4, wherein
 the lower valve housing is provided with a projecting portion that projects toward the diaphragm in the lower valve chamber; and
 a periphery of the hole portion in the diaphragm is in contact with the projecting portion.

10. The fluid control apparatus according to claim 9, wherein the upper valve chamber, the lower valve chamber, and the projecting portion each have a cylindrical or substantially cylindrical shape when viewed from above in a direction perpendicular or substantially perpendicular to the diaphragm.

11. A fluid control apparatus comprising:
 a pump including:
  a cover plate including an ejection hole;
  a piezoelectric actuator including a vibrating plate, a piezoelectric element, and a reinforcement plate;
  a flexible plate including a suction hole; and
  a substrate including an opening portion; wherein
  the cover plate, the piezoelectric actuator, the flexible plate, and the substrate are sequentially stacked; and
  when the pump is driven, a fluid flows from the opening portion and the suction hole into a gap between the piezoelectric actuator and the flexible plate in the pump and is ejected from the ejection hole; and
 a valve including:
  a lower valve housing including a ventilation hole and a lower valve chamber;
  an upper valve housing including a connection port and an upper valve chamber; and
  a diaphragm including a hole portion allowing the lower valve chamber and the upper valve chamber to communicate with each other; wherein
  the lower valve housing, the diaphragm, and the upper valve housing are sequentially stacked;
 the pump and the valve are bonded to each other so that the ventilation hole and the ejection hole communicate with each other; and
 a portion of the upper valve housing that opposes the hole portion includes a flow channel formation portion that allows the hole portion and the connection port to communicate with each other when the hole portion comes into contact with the upper valve housing.

* * * * *